(12) United States Patent
Dirauf et al.

(10) Patent No.: US 8,632,246 B2
(45) Date of Patent: Jan. 21, 2014

(54) IRRADIATION SYSTEM

(75) Inventors: Franz Dirauf, Ebensfeld (DE); Franz Fadler, Hetzles (DE); Paul Weidner, Pressath (DE)

(73) Assignee: Siemens Aktiengesellschaft, München (DE)

( * ) Notice: Subject to any disclaimer, the term of this patent is extended or adjusted under 35 U.S.C. 154(b) by 28 days.

(21) Appl. No.: 13/099,340

(22) Filed: May 2, 2011

(65) Prior Publication Data

US 2012/0104283 A1     May 3, 2012

(30) Foreign Application Priority Data

May 3, 2010 (DE) .......................... 10 2010 019 017

(51) Int. Cl.
     *H05G 1/02*      (2006.01)

(52) U.S. Cl.
     USPC ............................ 378/197; 378/196; 378/198

(58) Field of Classification Search
     USPC ........ 250/491.1; 378/163, 195, 196, 197, 198
     See application file for complete search history.

(56) References Cited

U.S. PATENT DOCUMENTS

| | | | |
|---|---|---|---|
| 2,793,296 A | 5/1957 | Peterson, Jr. | |
| 2,950,394 A | 8/1960 | Stava et al. | |
| 4,727,564 A * | 2/1988 | Mekker et al. | 378/197 |
| 5,023,899 A | 6/1991 | Ohlson | |
| 5,572,567 A * | 11/1996 | Khutoryansky et al. | 378/197 |
| 5,636,259 A * | 6/1997 | Khutoryansky et al. | 378/197 |
| 5,734,694 A * | 3/1998 | Khutoryansky et al. | 378/197 |
| 6,155,713 A * | 12/2000 | Watanabe | 378/197 |
| 6,220,752 B1 * | 4/2001 | Csikos et al. | 378/197 |
| 7,263,172 B2 * | 8/2007 | Grunau | 378/163 |
| 7,331,712 B2 * | 2/2008 | Fischer et al. | 378/203 |
| 2005/0058257 A1 | 3/2005 | Fischer et al. | |
| 2008/0303457 A1 | 12/2008 | Maltz | |

FOREIGN PATENT DOCUMENTS

DE     10 2010 032 131 A1     1/2011

OTHER PUBLICATIONS

German Office Action dated Feb. 9, 2011 for corresponding German Patent Application No. DE 10 2010 019 017.9-54 with English translation.

* cited by examiner

*Primary Examiner* — Nikita Wells
*Assistant Examiner* — Johnnie L Smith
(74) *Attorney, Agent, or Firm* — Lempia Summerfield Katz LLC

(57) ABSTRACT

The present embodiments relate to a system for irradiating a patient. The system for irradiating the patient includes a horizontal guide and a vertical guide. The vertical guide is connected horizontally-adjustably to the horizontal guide. The system also includes a support element that is attached vertically-adjustably to the horizontal guide and a radiation unit including a radiation source. The radiation unit is arranged on the support element. The irradiation system may be expanded by three further degrees of freedom.

21 Claims, 7 Drawing Sheets

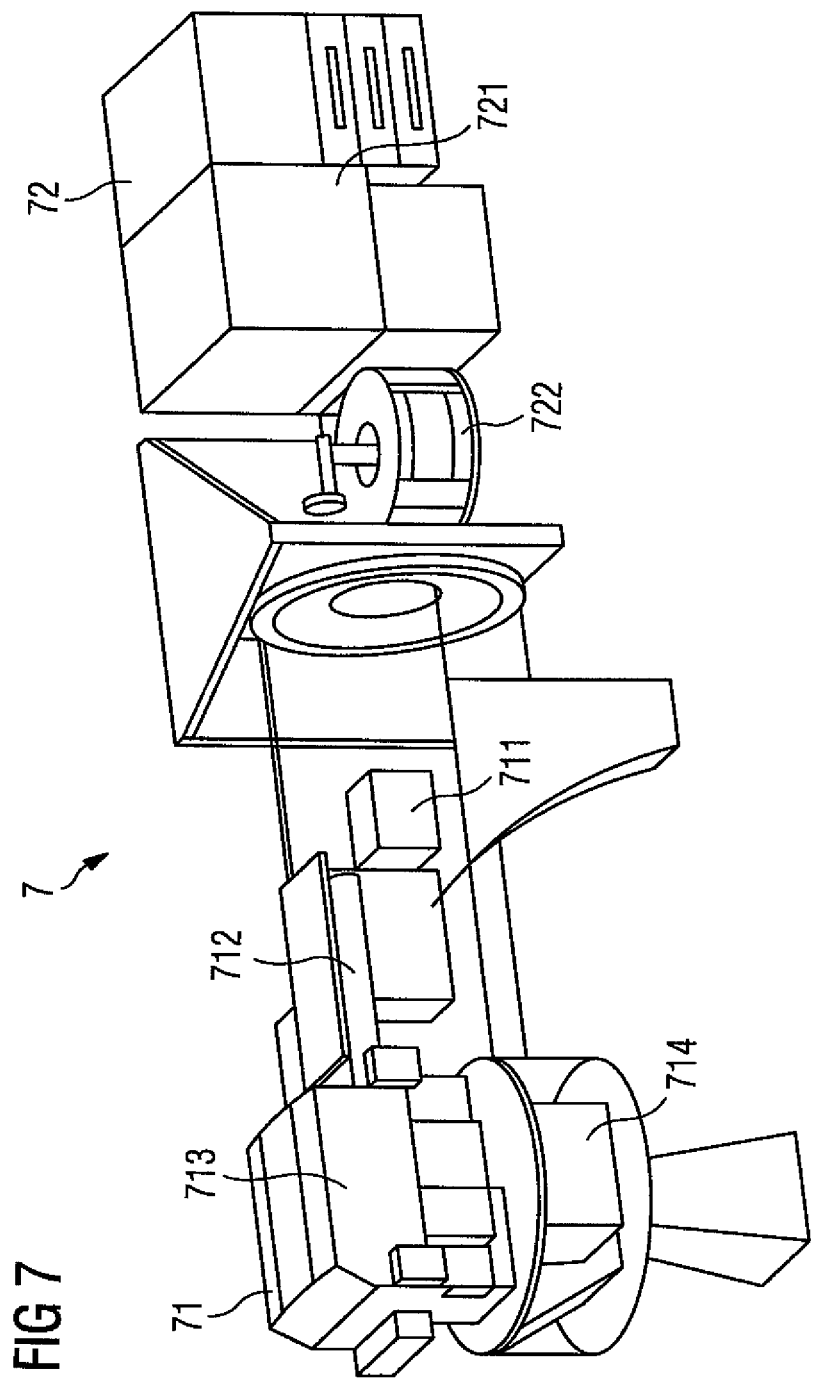

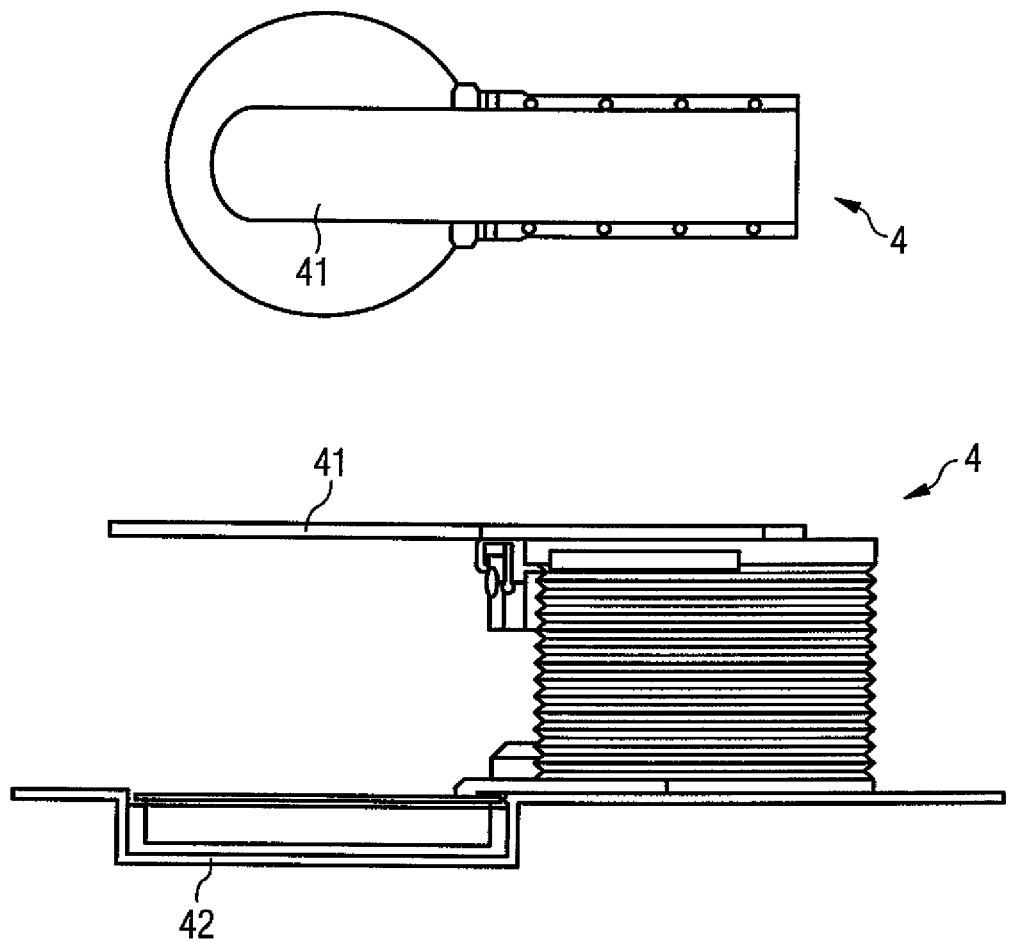

IRRADIATION SYSTEM

This application claims the benefit of DE 10 2010 019 017.9, filed May 3, 2010.

BACKGROUND

The present embodiments relate to a system for irradiating a patient.

The irradiation of patients using X-rays is a widely used diagnostic and therapeutic procedure in medicine. Typical systems for diagnosis of illnesses using X-rays are computer tomographs, C-arm devices and mammography devices. The radiation used in such systems may lie in the energy range of several keV.

For therapeutic applications, X-rays with a higher energy may be used (e.g., MeV range). The energy of this radiation is high enough to destroy tumors or diseased tissue. Greater outlay is required to generate high-energy X-rays by comparison with generation of low-energy X-rays. Linear accelerators (e.g., Linacs) may be used to generate the high-energy X-rays. The structure of such a Linac is described, for example, in publication U.S. 2008/0303457 A1.

Irradiation systems that allow irradiation to be carried out from different directions are known. Such a system is shown in FIG. 1. A gantry 1 is attached to a support 2. Embedded in the gantry 1 is a linear accelerator, which allows the emission of X-rays via an opening 3. A patient to be treated is positioned on a patient positioning device 4. The irradiation system of FIG. 1 enables the gantry to be rotated around an axis. The system from FIG. 1 is shown again in FIG. 2, with the gantry 1 being rotated by an angle or to the vertical position by comparison with FIG. 1. A tumor may be irradiated with the system shown in FIGS. 1 and 2 from many different angles.

For irradiation treatments with irradiation from different directions, the beam strikes the tumor for each of the directions. In other words, the beams may intersect at a point lying in an area of the tissue to be irradiated. This is also referred to as the (mechanical) isocenter (e.g., an intersection point of beams that correspond to different irradiation positions).

SUMMARY AND DESCRIPTION

There is a need for more flexible irradiation devices with a degree of freedom that allows isocentric irradiation.

The present embodiments may obviate one or more of the drawbacks or limitations in the related art. For example, an irradiation system that is embodied flexibly and in a low-cost way in relation to irradiation from different directions may be specified.

A system for irradiation of a patient is provided. The irradiation may be of both a therapeutic and a diagnostic nature. The irradiation system of the present embodiments includes a radiation unit with a radiation source. The radiation source may include a linear accelerator, for example. The radiation unit is also provided with a horizontal guide and a vertical guide. The horizontal guide may be attached to a floor or a ceiling. The vertical guide is connected to the horizontal guide to allow horizontal adjustment (e.g., the horizontal guide allows the movement or displacement of the vertical guide in the horizontal direction). The horizontal guide and the vertical guide may be realized using rails, for example, on which cars or carriages run or are able to be moved. The vertical guide may be attached to the car or the carriage of the horizontal guide. A support element is attached to the horizontal guide. The support element is vertically adjustable. The support element may include a car or a carriage. The radiation unit with the radiation source is arranged on the support element. The radiation unit may include a radiating head, in which, for example, the linear accelerator is disposed. The radiation unit may include a second part in addition to the head. The second part includes switching elements for power supply (e.g., generator, transformers). The radiation unit may be attached directly to the support element. The radiation unit may be attached to the support element with an attaching device that allows further degrees of freedom for the movement of the radiation unit.

The present embodiments make flexible positioning of the radiation unit in two dimensions (e.g., horizontal and vertical) possible. The arrangement is highly stable since the radiation unit is disposed on the horizontal guide using the support element (e.g., the radiation unit is also mechanically supported by the support element). The arrangement of the present embodiments with a separate radiation unit allows further degrees of freedom to be provided at low cost.

In one embodiment, the radiation unit is disposed rotatably around an axis of rotation on the support element. The axis of rotation is substantially transversal or a substantially transversal axis. "Transversal" may be a transversal axis being orthogonal to the horizontal and vertical direction or axis. The term "substantially" may be understood such that a pivoting movement of the radiation unit may be provided, in accordance with which the axis of rotation is no longer orthogonal to the vertical axis or only approximately transversal. In other words, the axis of rotation is orthogonal both to the horizontal axis and the vertical axis in at least one position of the radiation unit. This further degree of freedom of the radiation unit allows the patient to be irradiated from different (lateral) directions. The irradiation functions of the system from FIG. 1 may be emulated or reproduced with the horizontal and vertical degree of freedom.

In one embodiment, the radiation unit is arranged so that the radiation unit may be pivoted around a pivot axis. The pivot axis may be horizontal in at least one position (e.g., in at least one position of the radiation unit, the pivot axis is a horizontal axis). Both an axis of rotation and a pivot axis may be provided, and the pivot axis also rotates around the axis of rotation during a rotation. In other words, the rotation or axis of rotation is realized using components that rotate along with a rotation of the radiation unit.

The vertical guide and the horizontal guide may each be implemented using two rails. In the case of the vertical guide, the support element may be attached to both of the two rails. The two rails may be configured so that space for motors or a driving device for moving or driving elements is present between the two rails or partly between the two rails. In one embodiment, a controller of the irradiation system is provided. The controller may be configured to coordinate the movement of the individual degrees of freedom or movement options so that in the course of an irradiation, during which the radiation unit changes position or orientation, an isocentric irradiation occurs.

In one embodiment, a system includes an irradiation system, a patient table that includes different degrees of freedom, and a controller for the different degrees of freedom of the irradiation system and the patient table. The controller of the overall system is configured so that an isocentric irradiation is possible.

BRIEF DESCRIPTION OF THE DRAWINGS

FIG. 7 shows one embodiment of an irradiation unit; and

FIG. 8 is a schematic diagram of one embodiment of a patient table.

DETAILED DESCRIPTION OF THE DRAWINGS

Figure 1:
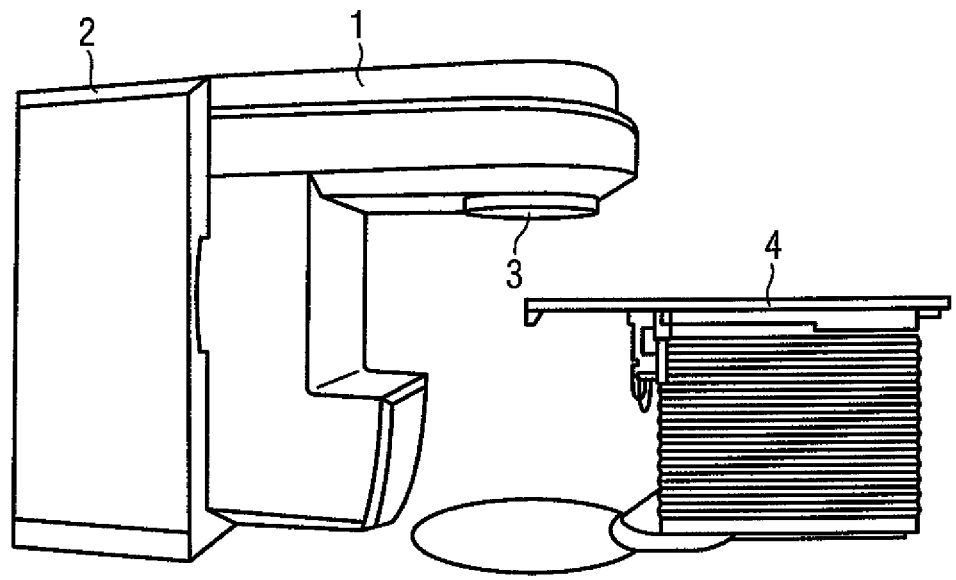
FIG. 1 an irradiation system.
Figure 2:
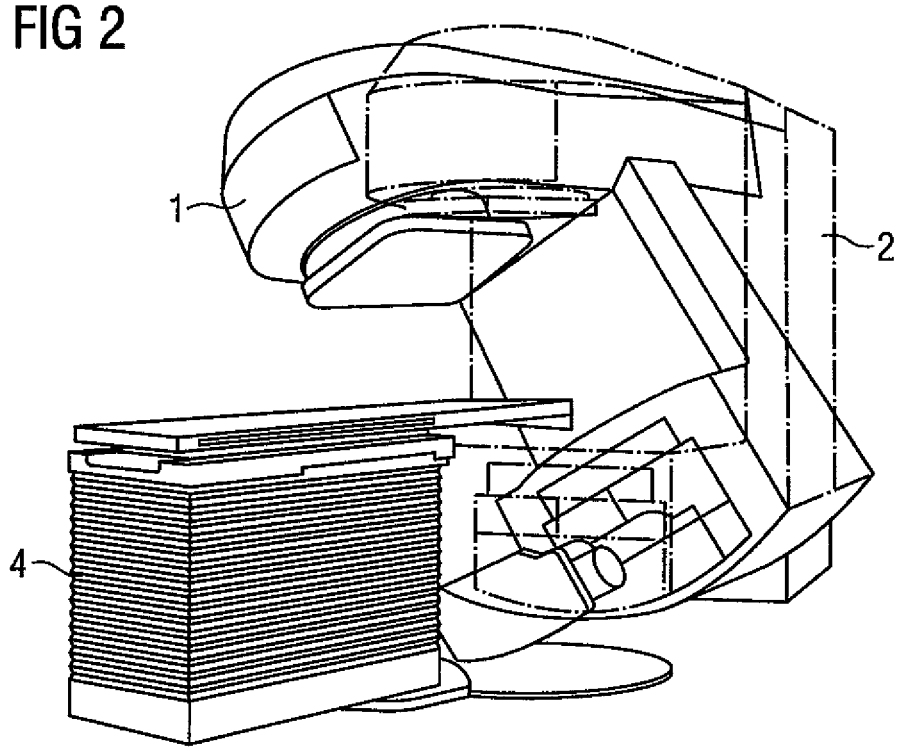
FIG. 2 shows the irradiation system from FIG. 1 with a pivoted gantry.

FIGS. 1 and 2 shows an irradiation system, in which one degree of freedom (e.g., rotation) of a radiation source is provided. Further degrees of freedom are relocated to a patient table 4 to allow patient positioning. Possible degrees of freedom of the patient table 4 are shown below with reference to FIG. 8.

Figure 3:
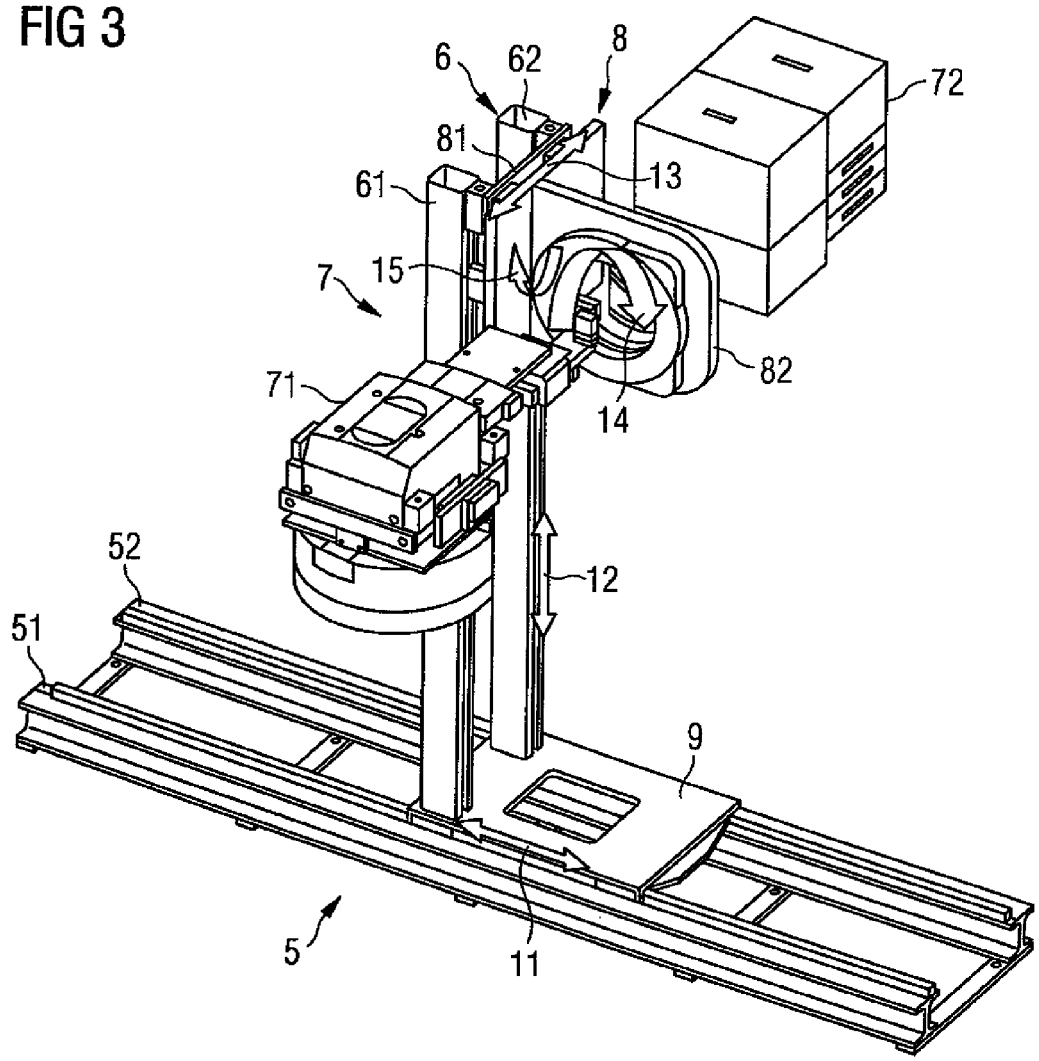
FIG. 3 shows one embodiment of an irradiation system.

FIG. 3 shows one embodiment of an irradiation system. The irradiation system is shown without cover panels (unlike FIGS. 1 and 2) in order to give a better idea of how the irradiation system functions. The entire irradiation system is based on a floor guide 5 (e.g., a horizontal guide) that is formed by two rails 51 and 52 (e.g., horizontal rails). In one embodiment, a ceiling guide may be provided instead of or in addition to the floor guide 5. A carriage 9 that supports a vertical guide 6 is placed on the two rails 51 and 52. The vertical guide 6 is formed by two rails 61 and 62. A device for driving the irradiation system may be provided between the two rails 51 and 52 or 61 and 62 or on the carriage 9. A support element 8 for supporting a radiation unit 7 is provided. The support element 8 may be driven along the vertical guide 6. This is realized by the support element 8 being formed by a carriage 81, on which a plate 82 with an opening (e.g., round) is arranged. The radiation unit 7 is arranged on the plate 82. The opening of the plate 82 is provided for the passage of connections between two parts 71 and 72 of the radiation unit 7. The connections may be provided for the transmission of energy (e.g., cables) and also for mechanical purposes (e.g., stability). The two parts 71 and 72 of the radiation unit 7 may have different functions (e.g., energy generation (72) or radiation generation (71)). This may be seen in greater detail with reference to FIG. 5. The weight of the two components 71 and 72 of the support unit 7 is at least partly compensated for in relation to an attachment point on the plate 82 (e.g., the design of the radiation unit 7 from substantially two parts reduces the load (torques occurring)).

The irradiation system shown in FIG. 3 has five degrees of freedom. One degree of freedom of movement or translation along a horizontal axis 11 is provided. The degree of freedom along the horizontal axis 11 is realized using the carriage 9. A translation in a vertical direction is also realized using the vertical guide 6 and the support element 8 (e.g., the carriage 81). A further degree of freedom is a translation along a transversal axis 13. This is realized, for example, by the plate 82 being movable transversely on the support element 8 (e.g., the carriage 81).

The transversal degree of freedom 13 may, for example, be implemented using a linear guide (e.g., with rails as guide elements) and a threaded spindle that converts the rotational movement of the motor into a linear movement. The radiation unit 7 may be rotated around a substantially transversal axis (e.g., degree of freedom 14). The term "substantially" may be that the axis is transversal in the position shown in the FIG. 3. For a pivoting of the radiation unit 7 (e.g., degree of freedom 15), the rotation 14 may not be precisely around a transversal axis but around an axis deviating from the transversal axis, depending on the tilt angle. The degree of rotational freedom 14 may, for example, be realized using a worm drive or a worm wheel. A degree of pivoting freedom 15, which shown in FIG. 3 with respect to a horizontal axis, is also provided.

In one embodiment, a corresponding pivot joint or the pivot axis rotates along with a rotation (e.g., degree of freedom 14). In other words, if a rotation of the radiation unit 7 from the position of FIG. 3 is undertaken (cf., FIGS. 4a and 4c), the pivot axis is no longer horizontal, but the pivoting essentially follows the direction of irradiation (e.g., vertical position of the pivot axis in FIG. 4a, approximately 45° to the horizontal in FIG. 4c). This degree of pivoting freedom may be realized, for example, using a lever mechanism and a crank.

All the degrees of freedom may interact so that an isocentric irradiation is realized. For example, degree of pivot freedom 15 and degree of transversal freedom 13 may be changed together. This is because a pivoting of the radiation unit 7 may cause a deviation from the isocenter, which may be compensated for by a shift along the transversal axis 13.

Figure 4A:
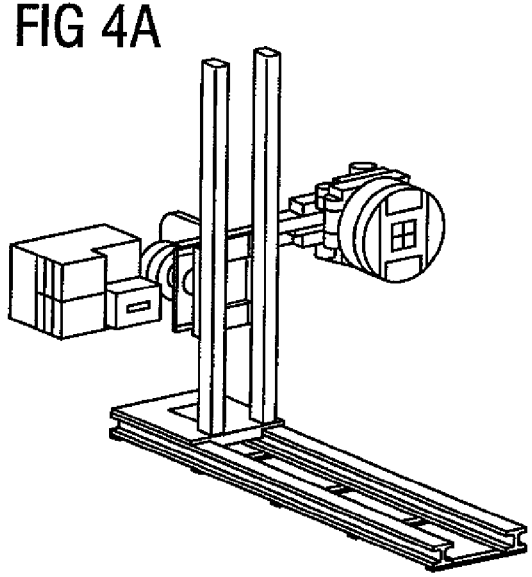
FIGS. 4a to 4c show different positions one embodiment of the irradiation system from FIG. 3.
Figure 4B:
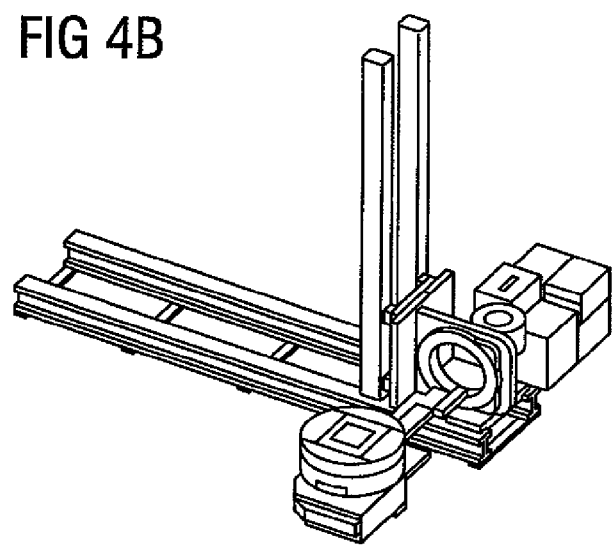
Figure 4C:
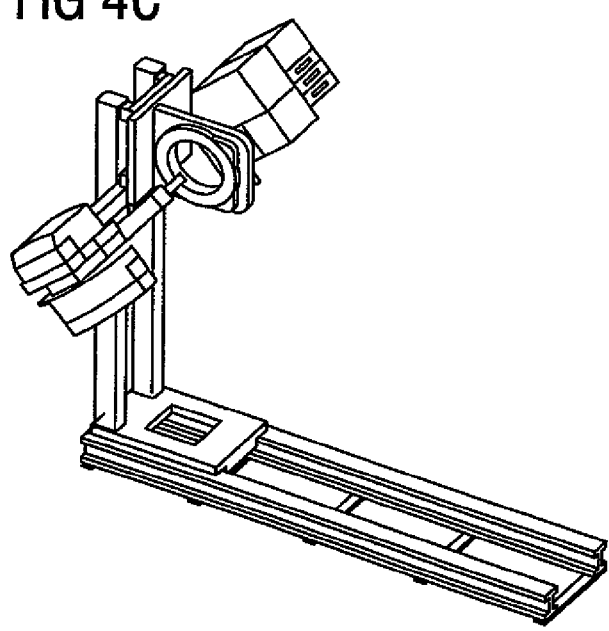

FIGS. 4a to 4c show the irradiation system in different positions. In the different positions, park positions, in which mechanical stresses are minimized and space for other measures is created in an area around the patient, may be defined. The park positions may appear as the position shown in FIG. 4b.

This irradiation direction has a comparatively simple overall mechanical structure. The overall mechanical structure manages with a single lifting column or vertical guide. An economic solution is thus involved. The horizontal guide 5, which may be attached to the floor or to the ceiling, produces a comparatively rigid structure (e.g., few deviations through bending of the material). The entire irradiation system may be parked to the side as shown in FIGS. 4a to 4c so that a plane above the horizontal rails 51 and 52 is freely accessible. Imaging systems (e.g., a CT gantry) may, for example, move into an area within the plane and carry out imaging without moving the patient table. Installations and alignment of the irradiation system may be undertaken in a comparatively simple manner. The five degrees of freedom of the kinematic enable static and dynamic deviations and deformations of the kinematic to be compensated for. This improves the accuracy of the positioning and reduces the effort involved in mechanical adjustments.

Figure 5:
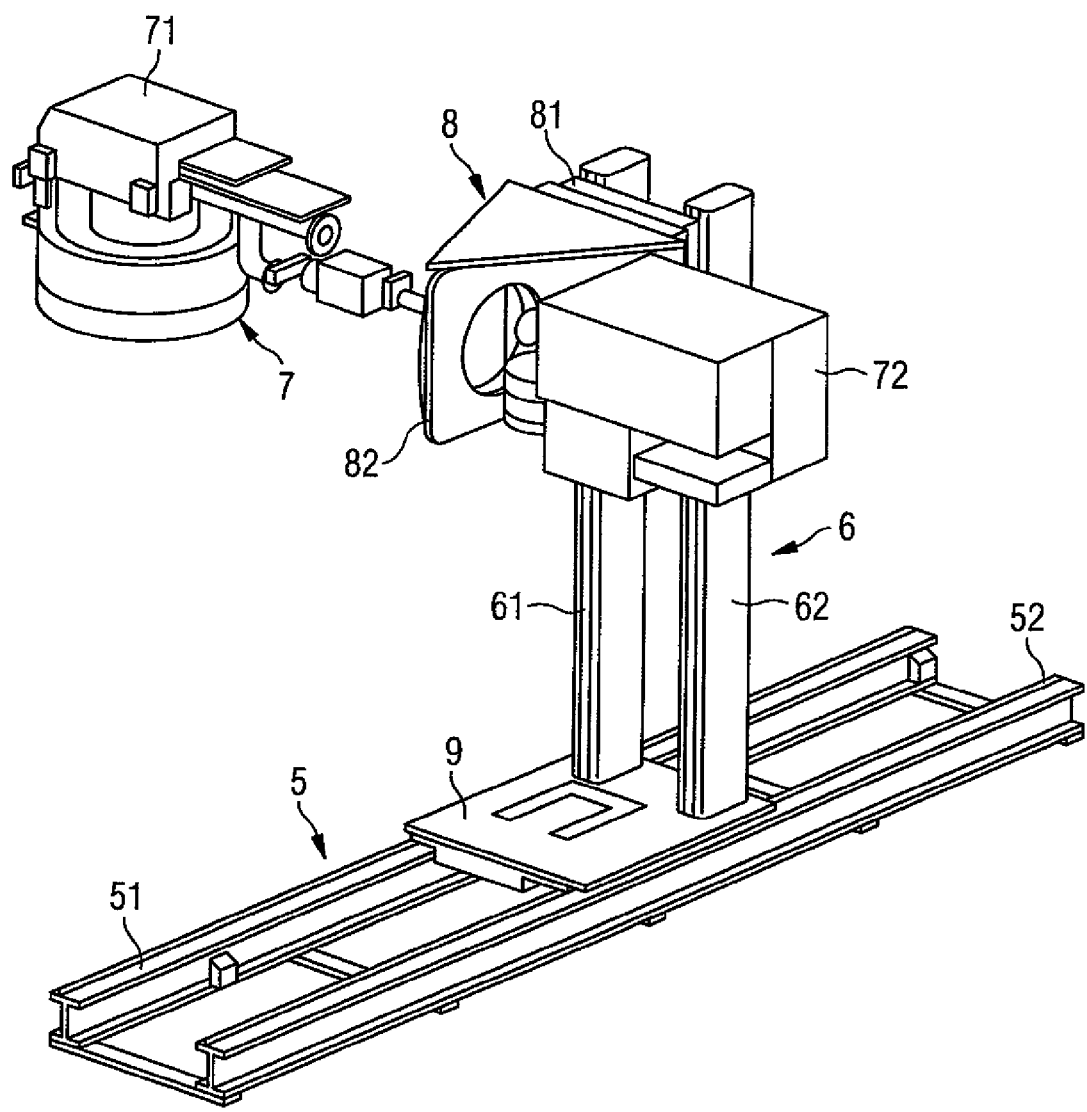
FIG. 5 shows one embodiment of the irradiation system in a different view from that shown in FIG. 3.
Figure 6:
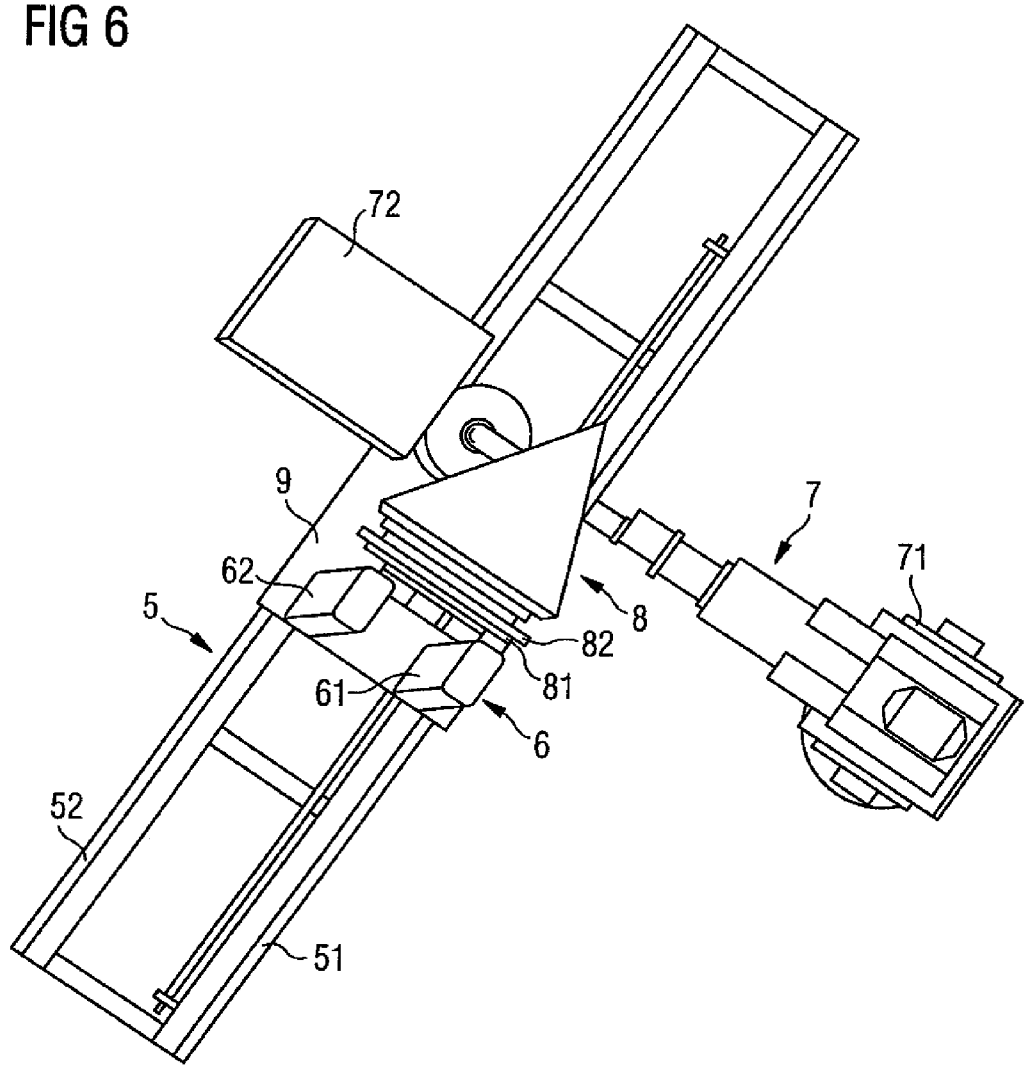
FIG. 6 is an overhead view of one embodiment of an irradiation system.

FIG. 5 and FIG. 6 show embodiments of the irradiation system viewed from different perspectives from those of FIG. 3 (e.g., FIG. 5 is at an angle from behind, FIG. 6 is from above). In one embodiment, the radiation unit 7 may be a separate component that may be inserted into the irradiation system. The position of the radiation unit 7 may be adapted flexibly using the degrees of freedom provided by irradiation system depending on requirements or in accordance with an irradiation plan.

FIG. 7 shows one embodiment of the radiation unit 7, which may be used in the irradiation system. The radiation unit 7 includes two parts 71 and 72 (e.g., a first part 71 and a second part 72). The first part 71, which may also be referred to as the radiation head, includes the typical functions for radiation generation (e.g., a circulator 711, a linear accelerator 712, a magnet for shielding and for redirecting a beam 713, and a multileaf collimator 714). The second part 72 essentially includes components for energy generation and modulation 721 and a magnetron 722 (e.g., a vacuum runtime tube for generating electromagnetic radiation in the microwave range). The magnetron represents a generator for high frequency. The construction of the radiation unit 7 allows the radiation unit 7 to use the kinematic shown in FIG. 3 efficiently. In addition to the degrees of freedom of the radiation unit 7, as are shown in FIG. 3, degrees of freedom of the patient table used may be provided.

FIG. 8 shows a schematic of an overhead view and a side view of a patient table 4 having various degrees of freedom. As shown in the lower diagram, the patient table 4 is let into the floor and may be rotated around a base 42. A support surface or a board 41, on which the patient lies in the horizontal direction, may be moved. These and further possible degrees of freedom of the patient table 4 (e.g., a vertical degree of freedom) may be integrated into the irradiation system. A common controller (not shown in FIG. 8) for the irradiation device and the patient bed 4 regulates all degrees of freedom for an isocentric irradiation so that the beam passes through the isocenter.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A device for irradiating a patient, the device comprising:
    a horizontal guide;
    a vertical guide that is connected horizontally-adjustably to the horizontal guide;
    a support element that is attached vertically-adjustably to the vertical guide, a part of the support element comprising a first side, a second side, and an opening extending from the first side to the second side; and
    a radiation unit comprising a radiation source, the radiation unit being attached to the support element,
    wherein the radiation source comprises a linear accelerator,
    wherein the radiation unit comprises two parts, the weight of the two parts being at least partly compensated for in relation to an attachment point on the support element, and
    wherein a first part of the two parts is arranged closer to the first side than the second side, and a second part of the two parts is arranged closer to the second side than the first side.

2. The device as claimed in claim 1, wherein the support element comprises a vertically movable carriage or car.

3. The device as claimed in claim 1, wherein the horizontal guide is configured to attach to a ceiling or to a floor of a room.

4. The device as claimed in claim 1, wherein the radiation unit is arranged rotatably around an axis of rotation transversal in at least one position of the radiation unit on the support element.

5. The device as claimed in claim 1, wherein the radiation unit is arranged for pivoting around a pivot axis.

6. The device as claimed in claim 5, wherein the radiation unit is arranged rotatably on the support element around an axis of rotation transversal in at least one position of the radiation unit, and
    wherein the radiation unit is configured to pivot such that a corresponding pivoting axis is also rotated during a rotation of the radiation unit.

7. The device as claimed in claim 1, wherein the vertical guide comprises two rails, to which the support element is attached.

8. The device as claimed in claim 2, wherein the vertical guide is attached to the vertically movable carriage or car operable to be moved along the horizontal guide.

9. The device as claimed in claim 1, further comprising a controller configured to control the device through coordinated movements in accordance with movements of the device within an isocentric irradiation.

10. An irradiation system comprising:
    a device for irradiating a patient, the device comprising:
        a horizontal guide;
        a vertical guide that is connected horizontally-adjustably to the horizontal guide;
        a support element that is attached vertically-adjustably to the vertical guide, a part of the support element comprising a first side, a second side, and an opening extending from the first side to the second side; and
        a radiation unit comprising a radiation source, the radiation unit being attached to the support element, wherein the radiation source comprises a linear accelerator, wherein the radiation unit comprises two parts, the weight of the two parts being at least partly compensated for in relation to an attachment point on the support element, and wherein a first part of the two parts is arranged closer to the first side than the second side, and a second part of the two parts is arranged closer to the second side than the first side;
    a patient table operable to move in at least one direction; and
    a controller configured to control the irradiation system through coordinated movements in accordance with movements of the device and of the patient table in an isocentric irradiation.

11. The irradiation system as claimed in claim 10, wherein the support element comprises a vertically movable carriage or car.

12. The irradiation system as claimed in claim 1, wherein the horizontal guide is configured to attach to a ceiling or to a floor of a room.

13. The irradiation system as claimed in claim 1, wherein the radiation unit is arranged rotatably around an axis of rotation transversal in at least one position of the radiation unit on the support element.

14. The irradiation system as claimed in claim 1, wherein the radiation unit is arranged for pivoting around a pivot axis.

15. The irradiation system as claimed in claim 14, wherein the radiation unit is arranged rotatably on the support element around an axis of rotation transversal in at least one position of the radiation unit, and wherein the radiation unit is configured to pivot such that a corresponding pivoting axis is also rotated during a rotation of the radiation unit.

16. The irradiation system as claimed in claim 10, wherein the vertical guide comprises two rails, to which the support element is attached.

17. The irradiation system as claimed in claim 11, wherein the vertical guide is attached to the vertically movable carriage or car operable to be moved along the horizontal guide.

18. The irradiation system as claimed in claim 10, further comprising a controller configured to control the device through coordinated movements in accordance with movements of the device within an isocentric irradiation.

19. The device as claimed in claim 2, wherein the radiation unit is arranged for pivoting around a pivot axis.

20. The device as claimed in claim 1, wherein the radiation unit is arranged rotatably on the support element around an axis of rotation transversal in at least one position of the radiation unit, and
    wherein the radiation unit is configured to pivot such that a corresponding pivoting axis is also rotated during a rotation of the radiation unit.

21. The device as claimed in claim 1, wherein the part of the support element is a plate,
 wherein the support element comprises a carriage, the carriage being attached vertically-adjustably to the vertical guide, the plate being arranged on the carriage, and
 wherein the two parts of the radiation unit are arranged on the plate.

\* \* \* \* \*